United States Patent
Borck et al.

(10) Patent No.: US 8,728,496 B2
(45) Date of Patent: *May 20, 2014

(54) FUNCTIONALIZED RGD PEPTIDOMIMETICS AND THEIR MANUFACTURE, AND IMPLANT HAVING A COATING CONTAINING SUCH FUNCTIONALIZED RGD PEPTIDOMIMETICS

(75) Inventors: Alexander Borck, Aurachtal (DE); Matthias Gratz, Erlangen (DE); Horst Kessler, Garching (DE); Michael Joner, Puchheim (DE); Florian Rechenmacher, Munich (DE); Stefanie Neubauer, Munich (DE)

(73) Assignee: Biotronik AG, Buelach (CH)

( * ) Notice: Subject to any disclaimer, the term of this patent is extended or adjusted under 35 U.S.C. 154(b) by 165 days.

This patent is subject to a terminal disclaimer.

(21) Appl. No.: 13/292,498

(22) Filed: Nov. 9, 2011

(65) Prior Publication Data

US 2012/0121658 A1    May 17, 2012

Related U.S. Application Data

(60) Provisional application No. 61/412,804, filed on Nov. 12, 2010.

(51) Int. Cl.
| | | |
|---|---|---|
| *A61F 2/82* | (2013.01) | |
| *B05D 1/00* | (2006.01) | |
| *A61K 9/00* | (2006.01) | |
| *A61K 38/14* | (2006.01) | |
| *C07K 5/078* | (2006.01) | |
| *A61K 38/05* | (2006.01) | |
| *C07K 9/00* | (2006.01) | |
| *C07K 19/00* | (2006.01) | |
| *C07K 5/11* | (2006.01) | |
| *A61L 33/04* | (2006.01) | |
| *A61K 38/06* | (2006.01) | |

(52) U.S. Cl.
USPC ........ 424/400; 623/1.46; 427/2.25; 514/20.9; 514/21.9; 514/21.91; 530/322; 530/323; 530/330; 536/20; 546/305

(58) Field of Classification Search
None
See application file for complete search history.

(56) References Cited

U.S. PATENT DOCUMENTS

| | | | |
|---|---|---|---|
| 2002/0004060 A1 | 1/2002 | Heublein et al. | |
| 2004/0098108 A1 | 5/2004 | Harder et al. | |
| 2009/0053280 A1 * | 2/2009 | Joner et al. ............ | 424/423 |

FOREIGN PATENT DOCUMENTS

| | | |
|---|---|---|
| DE | 197 31 021 | 1/1999 |
| DE | 102 53 634 | 5/2004 |

OTHER PUBLICATIONS

U.S. Appl. No. 13/292,522, filed Nov. 9, 2011, titled Functionalized RGD Peptidomimetics and Their Manufacture, and Implant Having a Coating Containing Such Functionalized RGD Peptidomimetics, Alexander Borck et al., (not yet published).

* cited by examiner

*Primary Examiner* — Ernst Arnold
*Assistant Examiner* — Jianfeng Song
(74) *Attorney, Agent, or Firm* — Greer, Burns & Crain, Ltd.

(57) ABSTRACT

At least some embodiments of the invention relates to an implant having a coating that contains or is composed of a functionalized RGD peptidomimetic RGD-P1 having the formula (1) and/or a functionalized RGD peptidomimetic RGD-P2 having the formula (2), and an associated manufacturing method.

19 Claims, No Drawings

FUNCTIONALIZED RGD PEPTIDOMIMETICS AND THEIR MANUFACTURE, AND IMPLANT HAVING A COATING CONTAINING SUCH FUNCTIONALIZED RGD PEPTIDOMIMETICS

CROSS REFERENCE

The present application claims priority on U.S. Provisional Application No. 61/412,804 filed on Nov. 12, 2010, which application is incorporated by reference herein.

TECHNICAL FIELD

The invention relates to functionalized RGD peptidomimetics and an associated manufacturing method, and to an implant having a coating containing such RGD peptidomimetics.

BACKGROUND

Implants are utilized in modern medical technology in a variety of embodiments, including for example implants that perform a support function, such as stents, implants that perform a control function e.g. electrodes and implants that perform a measurement or monitoring function (e.g. sensors). Implants can be used for example to support vessels, hollow organs, and ductal systems (endovascular implants, e.g. stents), to fasten and temporarily fix tissue implants and tissue transplants in position, as well as for orthopedic purposes such as pin, plate, or screw and others. The stent is a form of an implant that is used particularly frequently.

Stent implantation has become established as one of the most effective therapeutic measures for treating vascular disease. Stents are used to provide support in a patient's hollow organs. To this end, stents of a conventional design have a filigree support structure composed of metallic struts; the support structure is initially present in a compressed form for insertion into the body, and is expanded at the application site. One of the main applications of stents of this type is to permanently or temporarily widen and hold open vasoconstrictions, in particular constrictions (stenoses) of the coronary arteries. In addition, aneurysm stents are known, for example, which are used to support damaged vascular walls.

Many stents include a circumferential wall having a support force that suffices to hold the constricted vessel open to the desired extent; many stents also include a tubular base body through which blood continues to flow without restriction. The circumferential wall is typically formed by a latticed support structure that enables the stent to be inserted, in a compressed state having a small outer diameter, until it reaches the constriction in the particular vessel to be treated, and to be expanded there, for example using a balloon catheter, to the extent that the vessel finally has the desired, increased inner diameter.

The implant, in particular the stent, has a base body composed of an implant material. An implant material is a non-living material that is used for a medical application and interacts with biological systems. A prerequisite for the use of a material as an implant material that comes in contact with the body environment when used as intended is its biocompatibility.

"Biocompatibility" refers to the capability of a material to evoke an appropriate tissue response in a specific application. This includes an adaptation of the chemical, physical, biological, and morphological surface properties of an implant to the recipient tissue, with the objective of achieving a clinically desired interaction. The biocompatibility of the implant material is furthermore dependent on the time sequence of the response of the biosystem in which the implant is placed. For example, irritations and inflammations, which can cause tissue changes, occur over the relative short term. Biological systems therefore respond differently depending on the properties of the implant material. Depending on the response of the biosystem, implant materials can be subdivided into bioactive, bioinert, and degradable/resorbable materials.

Implant materials include polymers, metallic materials, and ceramic materials (as coating, for example). Biocompatible metals and metal alloys for permanent implants can contain, for example, stainless steels (e.g. 316L), cobalt-based alloys (e.g. CoCrMo casting alloys, CoCrMo forging alloys, CoCrWNi forging alloys, and CoCrNiMo forging alloys), pure titanium and titanium alloys (e.g. CP titanium, TiAl6V4 or TiAl6Nb7), and gold alloys. In the field of biocorrodible stents, the use of magnesium or pure iron and biocorrodible base alloys of the elements magnesium, iron, zinc, molybdenum, and tungsten is proposed.

A biological response to polymeric, ceramic, or metallic implant materials depends on the concentration, duration of exposure, and type of supply. The presence of an implant material often evokes inflammatory responses which can be triggered by mechanical irritations, chemical substances, or metabolites. The inflammatory process is typically accompanied by the immigration of neutrophil granulocytes and monocytes through the vascular walls, the immigration of lymphocyte effector cells with the formation of specific antibodies to the inflammatory stimulus, activation of the complement system with the release of complement factors which act as mediators, and, ultimately, activation of blood coagulation. An immunological response is usually closely associated with the inflammatory response and can lead to sensitization and the development of allergies. Known metallic allergens include nickel, chromium, and cobalt which are also used in many surgical implants as alloying constituents. A problem associated with the implantation of a stent in a blood vessel is in-stent restenosis due to excessive neointimal growth caused by a strong proliferation of arterial smooth muscle cells and a chronic inflammatory response.

It is known that a greater level of biocompatibility can be achieved by coating implant materials with particularly tissue-compatible materials. These materials are usually organic or synthetic-polymeric in nature and are partially of natural origin. Further strategies for preventing restenosis focus on inhibiting proliferation using medication e.g. treatment using cytostatic agents. The active ingredients can be provided e.g. on the implant surface in the form of a coating that releases an active ingredient.

It is furthermore known that the RGD triad (Arg-Gly-Asp) serves many integrins as a primary recognition site for proteins of the extracellular matrix. Peptides that contain this sequence can therefore mimic the ligands of these integrins and bind thereto.

Due to the fact that RGD peptides are selective antagonists for integrins, their medical relevance—or the medical relevance of peptidomimetics derived therefrom—is the subject of research.

SUMMARY

The present invention provides an implant having a coating, wherein the coating contains or is composed of a functionalized RGD peptidomimetic RGD-P1 having the formula (1):

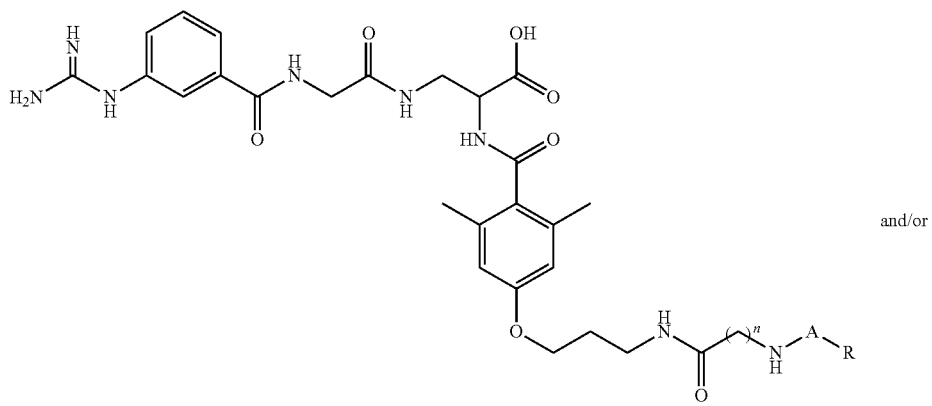

(1)

and/or a functionalized RGD peptidomimetic RGD-P2 having the formula (2):

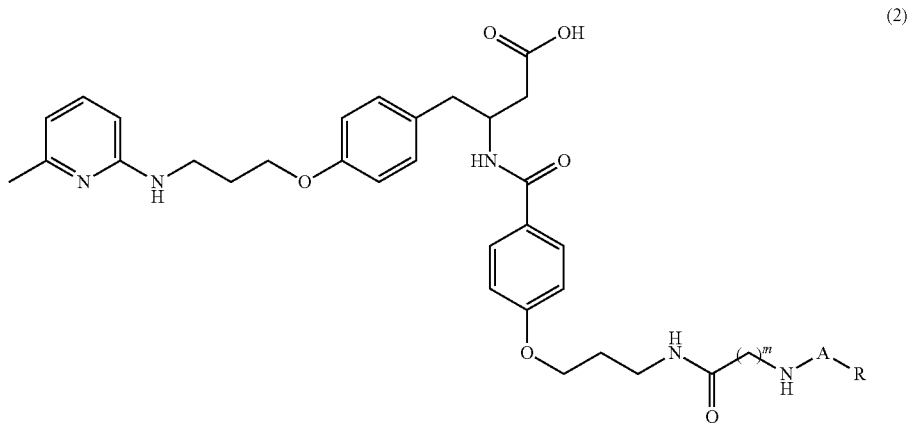

(2)

A, independently of one another, stands for a coupling group selected from 1,4-phenylene diisothiocyanate, 1,4-phenylene diisocyanate, 1-isothiocyanato-4-isocyanatobenzene, N,N'-carbonyldiimidazole and/or disulfosuccinimidyl-tartrate. The coupling group is preferably 1,4-phenylene diisothiocyanate, 1,4-phenylene diisocyanate, 1-isothiocyanato-4-isocyanatobenzene.

R, independently of one another, stands for a polymeric group selected from chitosan and polylysine, wherein polylysine comprises poly-D-lysine and poly-L-lysine; polylysine is preferably poly-L-lysine.

n and m are 1 through 20.

This aspect of the invention is based on the finding, for example, that by using the coupling, according to the invention, to the polymers chitosan or polylysine, the functionalized RGD peptidomimetics that are obtained can be applied to an implant particularly advantageously as a thin layer, while their integrin specificity and their integrin binding capabilities are substantially maintained. If an implant having an active ingredient-releasing coating includes a layer containing or composed of the functionalized RGD peptidomimetic RGD-P1 according to formula (1) and/or RGD-P2 according to formula (2), e.g. in the form of a cover layer, the elution characteristics of the underlying base for the active ingredient is not changed or changed only to a minor extent.

promoted by the integrin binding of the functionalized RGD peptidomimetic, while no effects—or only negligible effects—on the properties of underlying layers result.

DETAILED DESCRIPTION

Cyclic RGD peptides (cRGD) or RGD peptidomimetics can be used as components of an implant coating. Loading polymer stents with integrin-binding cRGD peptides can reduce neointimal hyperplasia by attracting endothelial progenitor cells.

In terms of developing implants coated with a coating that releases active ingredients, in particular stents coated with active ingredients (which are referred to as drug eluting stents or DES), the use of cRGDs or RGD peptidomimetics is a promising approach to improving the compatibility of implants. The use of RGD peptidomimetics is desireable to improve the healing process. For longer-term developments, however, it can be desirable to release other active ingredients, e.g. rapamycin, from the coating. Adding RGD peptidomimetics subsequently to an existing coating system therefore can create a problem related to ensuring that the RGD peptidomimetics are provided on the surface of the implant at the earliest possible point in time, while ensuring that the elution characteristic of an active ingredient contained in a base of the coating underneath the surface does not change.

Otherwise, the elution characteristic of the active ingredient would have to be re-optimized, which is very difficult to do in isolated cases, and which makes it difficult to vary the system.

With these considerations in mind, embodiments of the present invention advantageously design the provision of RGD peptidomimetics on the surface of an implant such that the elution characteristic out the base layer situated underneath do not change or change in only an unsubstantial manner, for an active ingredient embedded in an underlying base layer. Furthermore, in at least some invention embodiments the recognition sites of the RGD peptidomimetics are accessible immediately after implantation, instead of their becoming exposed by the gradual degradation of the coating matrix. These are only some of the benefits and advantages achieved by embodiments of the invention.

An RGD peptidomimetic is understood to be a chemical compound that behaves substantially like the fundamental protein in terms of the binding properties to selected integrins, but differs from the fundamental protein in terms of structure. Peptidomimetics typically do not have a continuous peptide backbone composed of peptide bonds and are usually composed non-exclusively of proteinogenic amino acids.

In the present case, the functionalized RGD peptidomimetic is RGD-P1 having the formula (1) is a compound that has an integrin-binding domain that preferably binds to $a_5\beta_1$ integrin. The integrin-binding domain of RGD-P1 has the following structure:

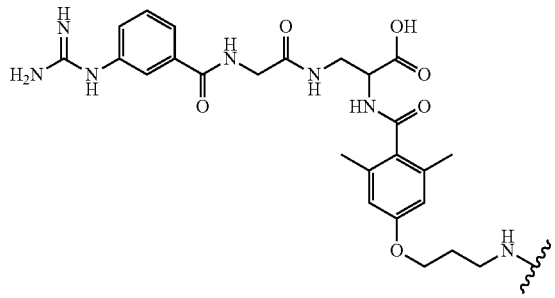 [SMILES: *NCCCOc1cc(C)c(C(=O)NC(CNC(=O)CNC(=O)c2cccc(NC(=N)N)c2)C(=O)O)c(C)c1]

The functionalized RGD peptidomimetic is RGD-P2 having the formula (2) is a compound that has an integrin-binding domain that preferably binds to $a_v\beta_3$ integrin. The integrin-binding domain of RGD-P2 has the following structure:

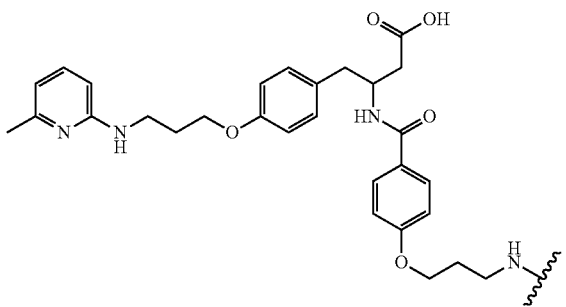 [SMILES: *NCCCOc1ccc(C(=O)NC(CC(=O)O)Cc2ccc(OCCCNc3cccc(C)n3)cc2)cc1]

The integrin-binding domains of the RGD peptidomimetics RGD-P1 and RGD-P2 are each adjoined by an aminoalkanoic acid which is used as a spacer.

The RGD peptidomimetics RGD-P1 and RGD-P2 are functionalized on the free amino group of the aminoalkanoic acid with a coupling group A which, in turn, is covalently bound via one of the free amino groups of the polymers to chitosan or polylysine.

The functionalized RGD peptidomimetic that is obtained is therefore a polymer based on chitosan or polylysine, wherein a specific RGD-based integrin-binding domain is coupled to one, several, or all free amino groups of chitosan or polylysine via coupling group A and an aminoalkanoic acid.

After implantation, to permit the most direct contact possible between the integrin-binding domains of the RGD peptidomimetics of the implant to integrins of surrounding cells, the implant according to at least some invention embodiments has the coating containing the functionalized RGD peptidomimetic RGD-P1 according to formula (1) and/or RGD-P2 according to formula (2) as the cover layer. A "cover layer" is understood to mean a layer that separates the implant together with any underlying layer(s) from the surroundings, at least in sections, as the outermost coating. According to a preferred embodiment, the cover layer overlays on an exterior side the coating of the implant which has an interior side that is adjacent to the base body of the implant.

Underneath the cover layer the implant can have a base layer that can be composed of one or a plurality of different layers. The cover layer covers the base layer at least partially or entirely. The base layer can include a layer that releases an active ingredient.

According to the invention, a coating refers to the application, at least in sections, of the components of the coating on the base body of the implant. Preferably, the coating covers the entire surface of the base body of the implant. A layer (either the cover layer or a base layer) thickness may be in the range of 1 nm to 100 μm, preferably 300 nm to 15 μm, although other thicknesses including smaller than 1 nm and greater than 100 μm may be used. The coating can be applied directly to the surface of the implant. The processing can be performed using standard methods for the coating with examples including but not limited to spraying, dipping, deposition, painting, and the like. The base layer can be composed of single-layered systems or multiple-layered systems (e.g. base coat layers, drug coat layers, or top coat layers). The base layer can be applied directly to the base body of the implant, or further layers can be provided therebetween. Methods for coating implants, for creating the base layer, and for creating the cover layer are known to a person skilled in the art, and include but are not limited to spraying, dipping, deposition, painting, and the like.

According to the invention, an active ingredient is a medicinal agent having a pharmaceutical effect, and which is used in the human body or animal body to cure, alleviate, prevent, or detect illness. Active ingredients include paclitaxel, sirolimus, rapamycin, rapamycin derivatives, and others. Others include active ingredients that act via the mTOR recognition site and RAS inhibitors, in particular those that prevent RAS adhesion to the cell membrane.

The implant according to the invention may be a stent, particularly preferably a biocorrodible stent. The stent can comprise a base body that contains or is composed of a biodegradable implant material. In the field of biocorrodible stents, the use of magnesium or pure iron and biocorrodible base alloys of the elements magnesium, iron, zinc, molybdenum, and tungsten may be made. In particular, the base body of the stent according to some invention embodiments can comprise or be composed of a biocorrodible magnesium alloy.

In this context, an alloy is understood to be a metallic microstructure having magnesium, iron, zinc or tungsten as the main component. The main component is the alloy component that comprises the largest weight component of the alloy. A portion of the main component is preferably more than 50% by weight, in particular more than 70% by weight.

The composition of the alloys of the elements magnesium, iron, zinc or tungsten can be selected such that they are biocorrodible. Within the scope of the invention, those alloys are referred to as being biocorrodible that degrade in a physiological environment, and therefore the entire implant or the part of the implant composed of the material loses its mechanical integrity. Artificial plasma is used as a test medium to test the corrosion behavior of a potential alloy, the artificial plasma being specified according to EN ISO 10993-15:2000 for biocorrosion tests (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). To perform the test, a sample of the alloy to be investigated is stored in a closed sample container with a defined quantity of the test medium at 37° C. Samples are taken at certain time intervals, which are based on the anticipated corrosion behavior, of a few hours to several months, and they are examined in a known manner for traces of corrosion. The artificial plasma according to EN ISO 10993-15:2000 corresponds to a blood-like medium and therefore provides a way to reproducibly adjust a physiological environment within the scope of the invention.

In many suitable biocorrodible metallic implant materials, the main component is an element of the group alkaline metals, alkaline-earth metals, iron, zinc, and aluminium. Alloys based on magnesium, iron and zinc are described as being particularly suitable. Minor constituents of the alloys can be manganese, cobalt, nickel, chromium, copper, cadmium, lead, tin, thorium, zirconium, silver, gold, palladium, platinum, silicon, calcium, lithium, aluminium, zinc and iron. Furthermore, one suitable biocorrodible magnesium alloy has a portion of magnesium>90%, yttrium 3.7-5.5%, rare-earth metals 1.5-4.4% and the rest<1%, which is suitable in particular for manufacturing a stent, with one example stent in the form of a self-expanding or balloon-expandable stent.

A further aspect of the invention is the provision of a method for manufacturing an aforementioned implant. The method comprises the steps:

Coat a stent with a layer that contains or is composed of chitosan and/or polylysin;

Covalent coupling of a primary amine contained in chitosan and/or polylysine with the coupling group A of a precursor of the RGD peptidomimetic RGD-P1 having the formula (3):

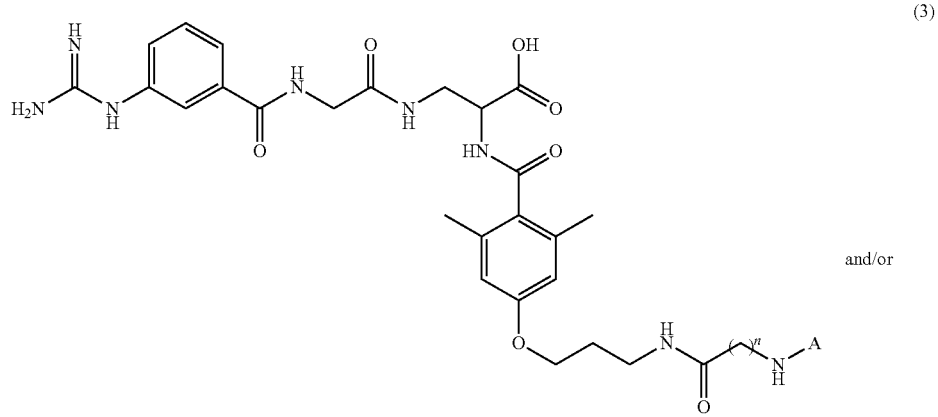

and/or a precursor of the RGD peptidomimetic RGD-P2 having the formula (4):

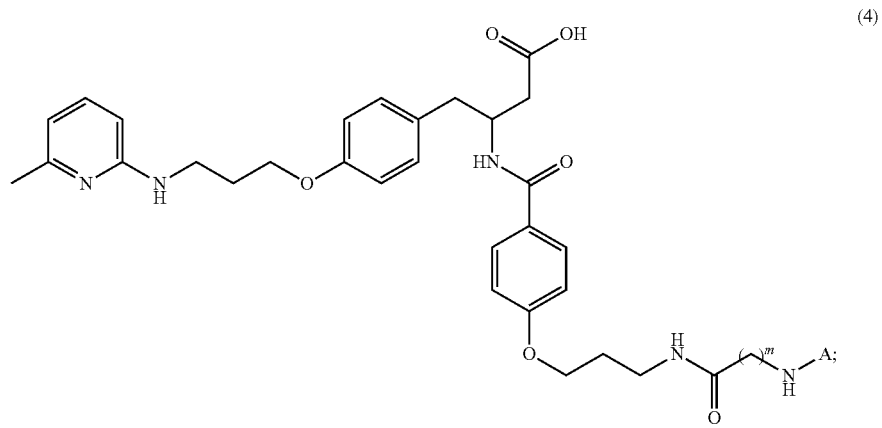

wherein A, independently of one another, stands for a coupling group selected from 1,4-phenylene diisothiocyanate, 1,4-phenylene diisocyanate, 1-isothiocyanato-4-isocyanatobenzene, N,N'-carbonyldiimidazole and/or disulfosuccinimidyltartrate, and n and m are 1 through 20 independently of one another.

Using the proposed method, it is possible e.g. to also coat existing active ingredient-releasing implants, stents, or systems with a cover layer containing the functionalized RGD peptidomimetics RGD-P1 and/or RGD-P2 after they are coated with the active ingredient itself.

A particular advantage is that the active ingredients that have already been coated onto the surface of the active ingredient-releasing implant can be provided with the coating containing the compounds according to the invention while maintaining their biological activity. Prior methods known to a person skilled in the art for coating a stent that has been previously coated (with sirolimus, by way of example) result in a partial destruction of the active ingredient, thereby reducing the biological activity of the implant.

The coating of the implant according to embodiments of the invention with a functionalized RGD peptidomimetic can be performed as follows. Chitosan or polylysine can be applied in a diluted aqueous solution, for example to a stent that may have also been pre-coated with a base material containing an active ingredient, using a spraying process or an immersion process. Subsequent coupling with precursors of the RGD peptidomimetic RGD-P1 and/or RGD-P2 takes place in the aqueous medium; when lipophilic active ingredients are used, there is no risk that the active ingredients bound in the base will elute in this medium and thereby lower the load of active ingredient.

A compound having the following structure can be used as the precursor to the RGD peptidomimetic RGD-P1:

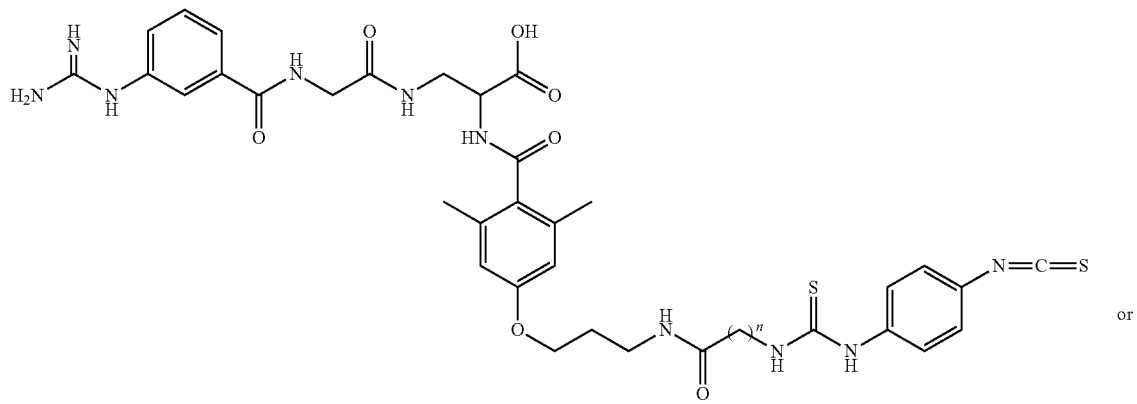

or

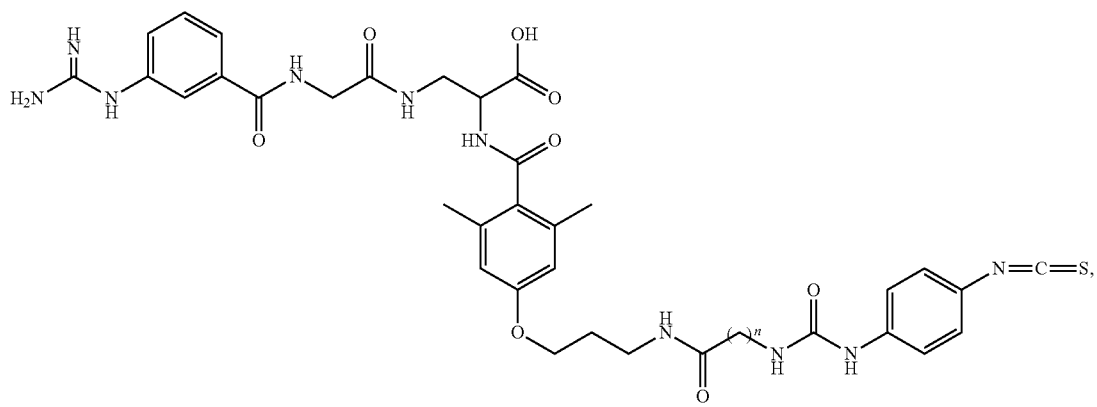

wherein n is 1 through 20, in particular 5.
In addition or as an alternative thereto, a compound having the following structure can be used as the precursor to the RGD peptidomimetic RGD-P2:
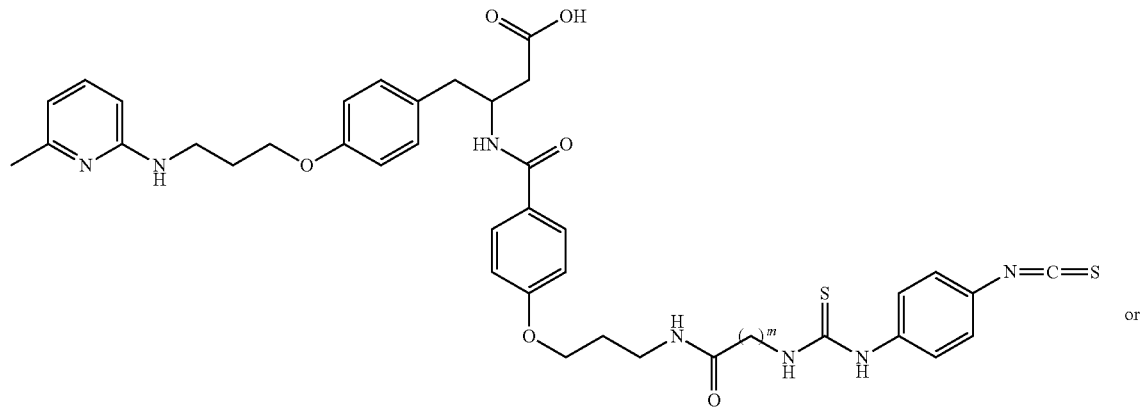
or
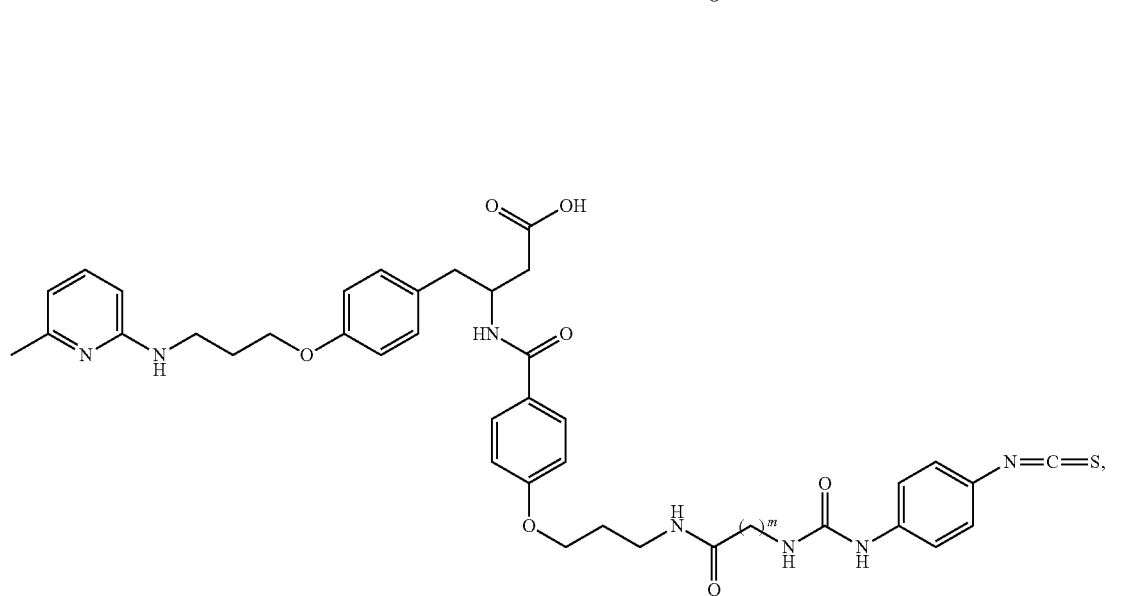
wherein m is 1 through 20, in particular 5.
In a further aspect, embodiments of the present invention provide compounds having: Formula (1)
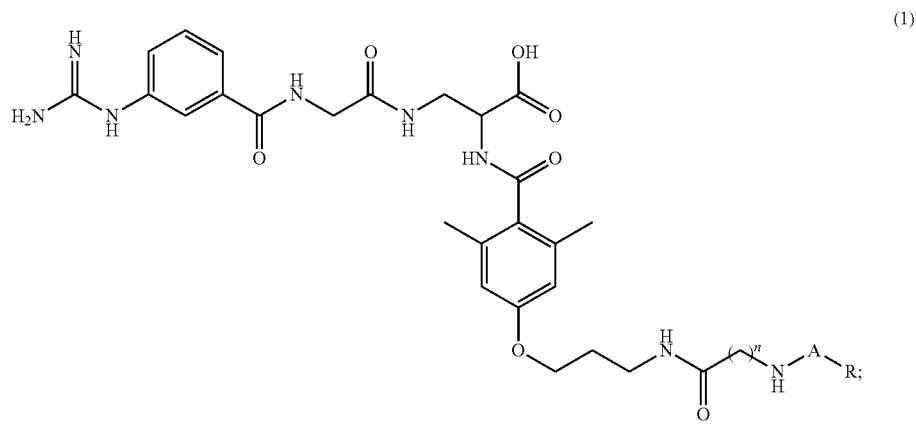
(1)

Formula (2)

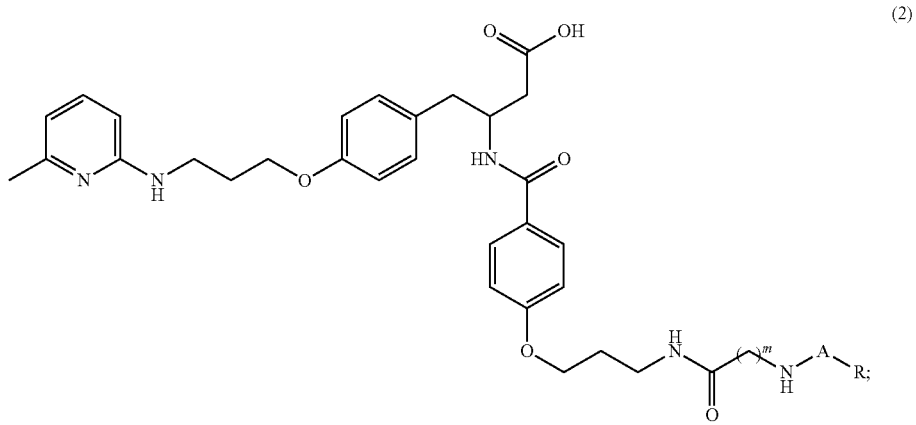

Formula (3)

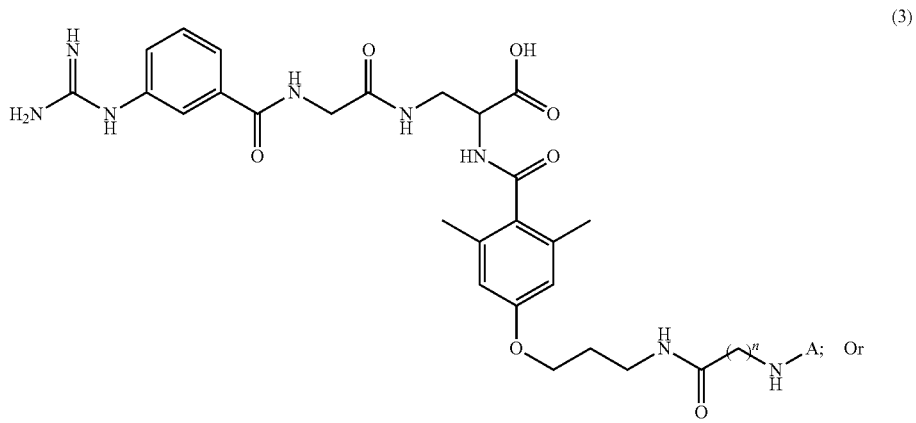

Formula (4)

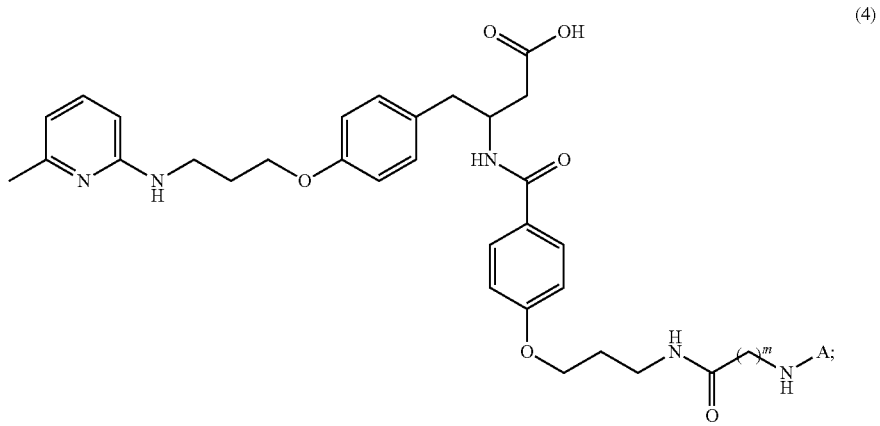

in which

A, independently of one another, stands for a coupling group selected from 1,4-phenylene diisothiocyanate, 1,4-phenylene diisocyanate, 1-isothiocyanato-4-isocyanatobenzene, N,N'-carbonyldiimidazole and/or disulfosuccinimidyl-tartrate; R, independently of one another, stands for chitosan or polylysine (D- or L-polylysine), and n and m, independently of one another, is 1 through 20, or
according to the structure:
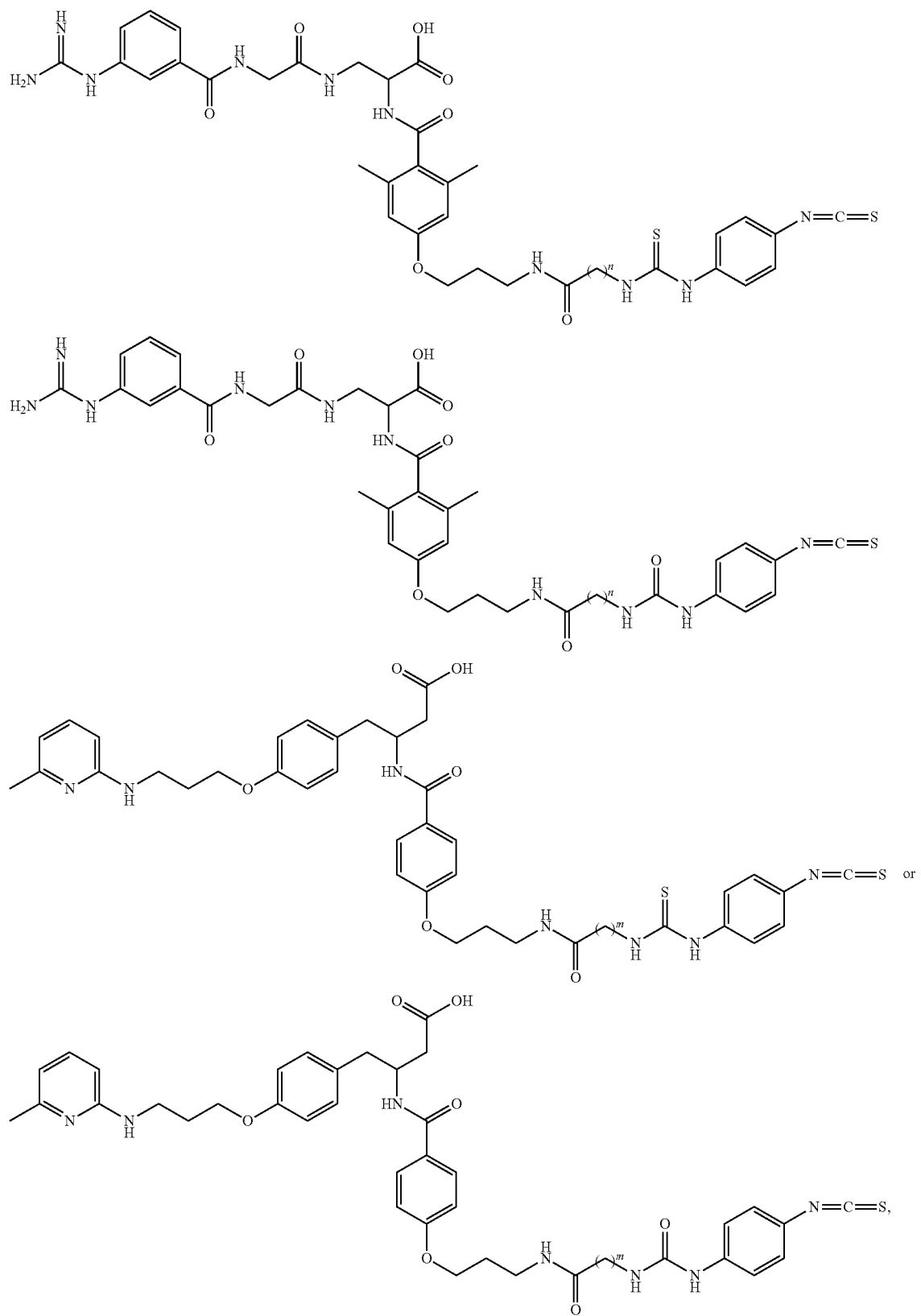

wherein n and m, independently of one another, is 1 through 20, in particular 5.

The aforementioned compounds according to embodiments of the invention can be used, for example, in a coating of an implant, in particular in the cover layer of an active ingredient-releasing stent, wherein the stent comprises a resorbable or permanent base body composed of a metallic or polymeric material with one or more layers under the cover layer.

Some aspects of the invention is explained below in greater detail below with reference to embodiments.

Reaction of the Compound Having the Formula (3) and (4) on a Chitosan Surface

Spray a stent comprising a coating of polylactide (PLLA) and sirolimus with a solution of chitosan in diluted acetic acid (0.3%). After drying, immerse the stent in a buffered (phosphate buffer 50 mM) aqueous solution of a precursor of the functionalized RGD peptidomimetic RGD-P1 having the formula (3) or a precursor of the functionalized RGD peptidomimetic RGD-P2 having the formula (4) (concentration: 5 mg/ml; pH 7; room temperature). After 1 hour, all amine groups of the chitosan have reacted with the reactive groups of the coupling groups.

The stent does not exhibit deviating elution kinetics for sirolimus. In contrast to stents that have been coated solely with PLLA and sirolimus, a first endothelial covering is visible just three days after implantation in the animal.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. An implant having a coating, wherein the coating comprises a functionalized RGD peptidomimetic RGD-P1 having the formula (1):

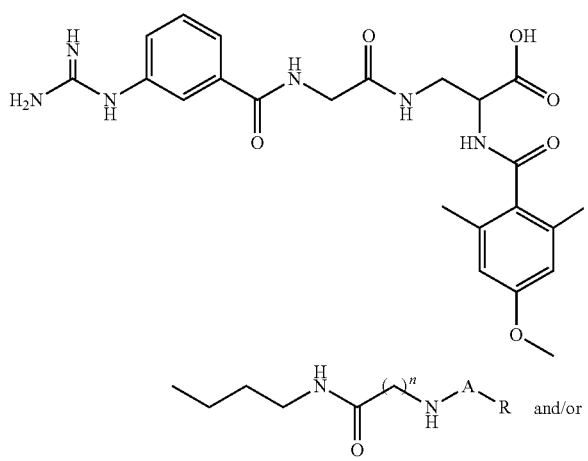

a functionalized RGD peptidomimetic RGD-P2 having the formula (2):

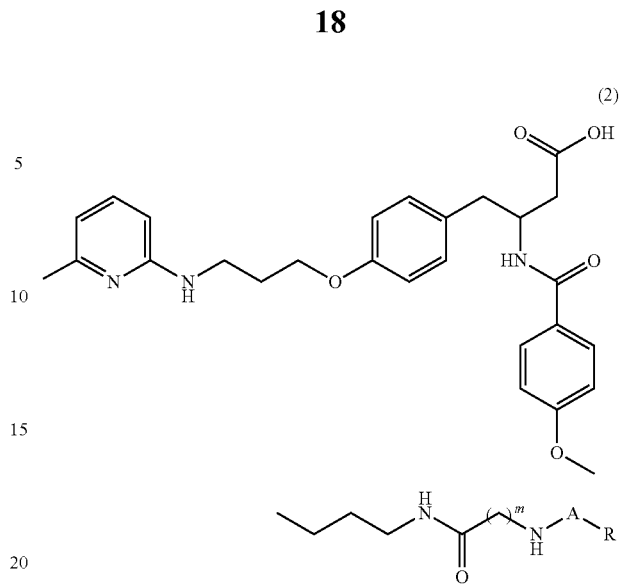

wherein A, independently of one another, stands for a coupling group selected from 1,4-phenylene diisothiocyanate, 1,4-phenylene diisocyanate, 1-isothiocyanato-4-isocyanatobenzene, N,N'-carbonyldiimidazole and/or disulfosuccinimidyltartrate; R, independently of one another, stands for chitosan or polylysine; wherein A is covalently linked to an amine group of R; and n and m, independently of one another, is 1 through 20.

2. The implant according to claim 1, wherein the coupling group is one or 1,4-phenylene diisothiocyanate, 1,4-phenylene diisocyanate, or 1-isothiocyanato-4-isocyanatobenzene.

3. The implant according to claim 1, wherein the coating is a cover layer.

4. The implant according to claim 3, and further comprising a base layer under the cover layer.

5. The implant according to claim 4, wherein the base layer includes a layer that releases an active ingredient.

6. The implant according to claim 5, in which the active ingredient is one or more of paclitaxel, sirolimus, and rapamycin.

7. The implant according to claim 1, wherein the implant is one of a stent, a sensor, and an electrode.

8. The implant according to claim 7, wherein the stent comprises a resorbable base body composed of a polymeric material.

9. A method for manufacturing an implant according to claim 1, wherein the method comprises the steps:

Coat a stent with a layer that comprises one or more of chitosan and polylysin;

Covalent coupling a primary amine contained in the one or more of chitosan and polylysine with the coupling group of one or more of a precursor of a RGD peptidomimetic RGD-P1 having the formula (3):

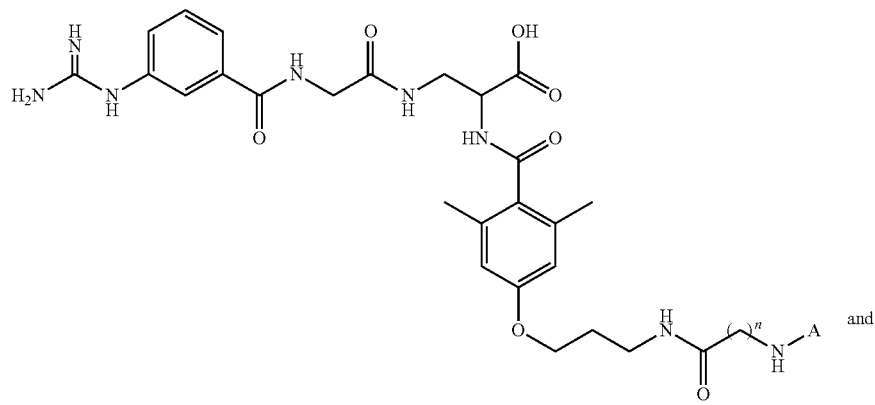

(3)

a precursor of the functionalized RGD peptidomimetic RGD-P2 having the formula (4):

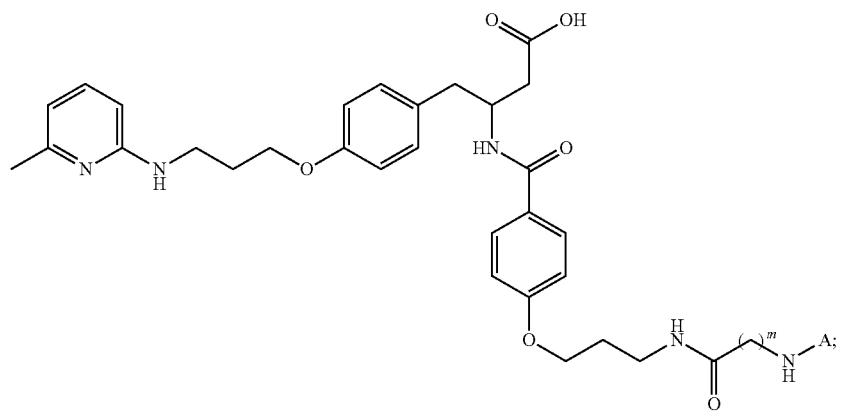

(4)

wherein A, independently of one another, stands for a coupling group selected from 1,4-phenylene diisothiocyanate, 1,4-phenylene diisocyanate, 1-isothiocyanato-4-isocyanatobenzene, N,N'-carbonyldiimidazole and/or disulfosuccinimidyltartrate, and n and m are 1 through 20 independently of one another.

10. The method according to claim 9, wherein the precursor to the functionalized RGD peptidomimetic RGD-P1 is a compound having the structure:

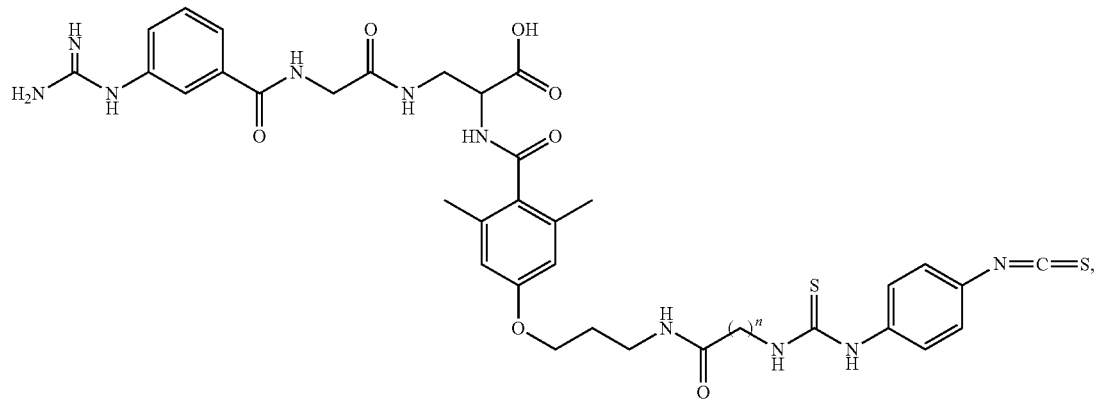
wherein n is 1 through 20.
11. The method according to claim 9, wherein the precursor to the functionalized RGD peptidomimetic RGD-P1 is a compound having the structure:
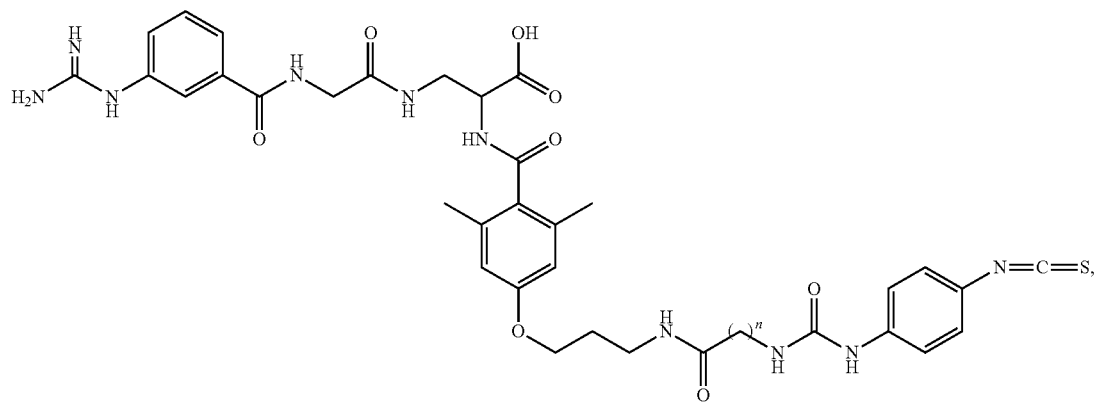
wherein n is 1 through 20.
12. The method according to claim 9, wherein the precursor to the functionalized RGD peptidomimetic RGD-P2 is a compound having the structure:
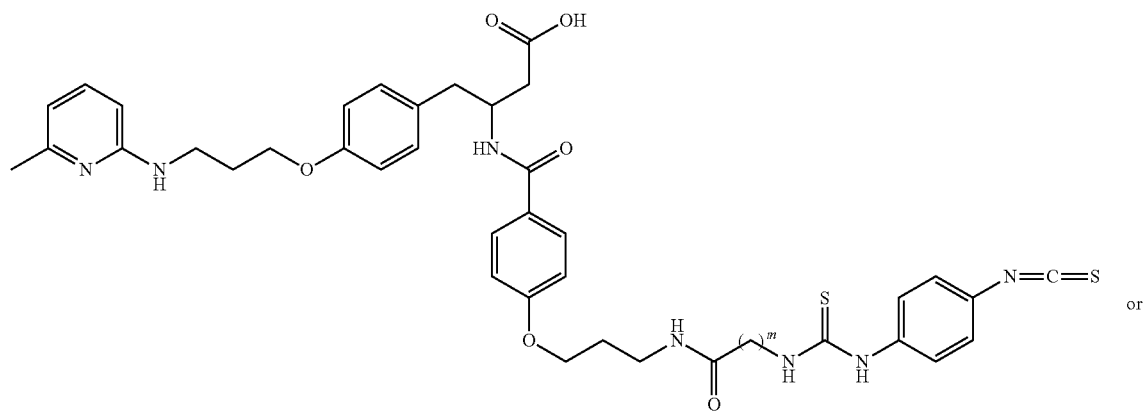
or -continued

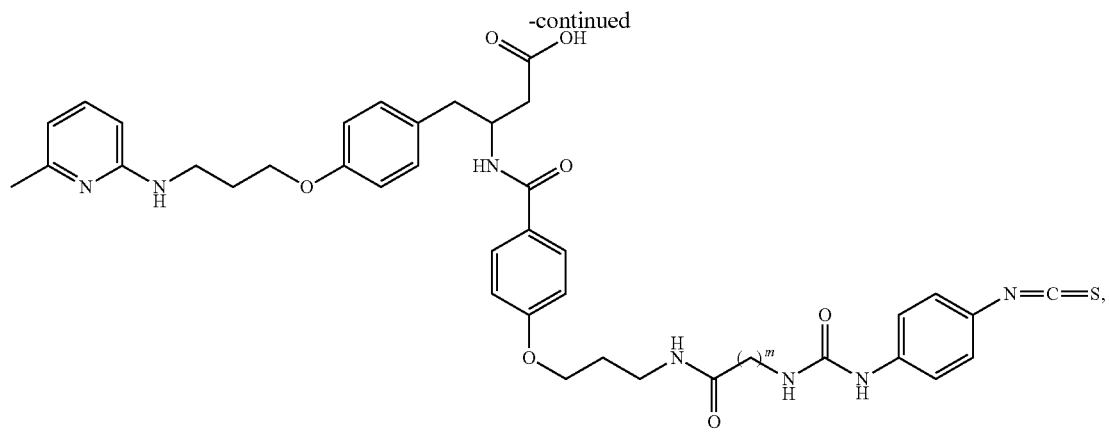

wherein m is 1 through 20.

13. The method according to claim 9, wherein n and m are 5, independently of one another.

14. The implant according to claim 7, wherein the stent comprises a permanent base body composed of a metallic material.

15. The implant according to claim 1, wherein the layer is a cover layer, and further comprising
a base layer underlying the cover layer, an active ingredient embedded in the base layer; and,
wherein the elution characteristic of the active ingredient in the base layer underneath the cover layer do not change with the presence of the cover layer as compared to having no cover layer present.

16. The implant as defined by claim 15 wherein the active ingredient is a rapamycin derivative.

17. The implant as defined by claim 1 wherein the cover layer thickness is between about 300 nm to 15 μm.

18. The implant as defined by claim 1 wherein the recognition sites of the RGD peptidomimetics are accessible immediately after implantation.

19. An implant having an active ingredient releasing coating, wherein the coating comprises at least one compound according to:

Formula (1)

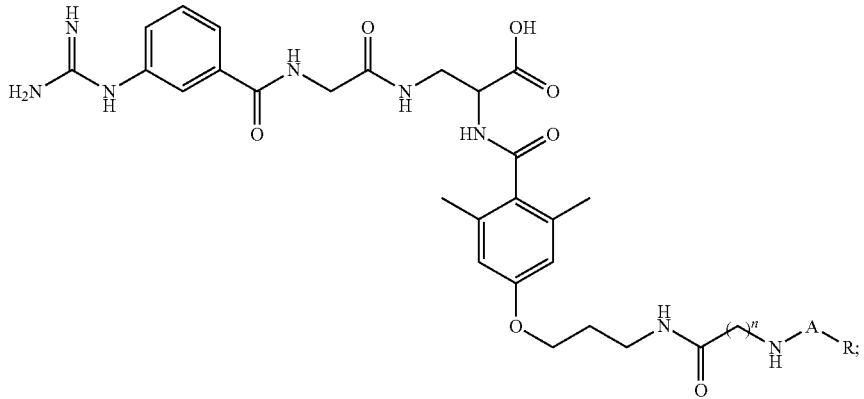

Formula (2)

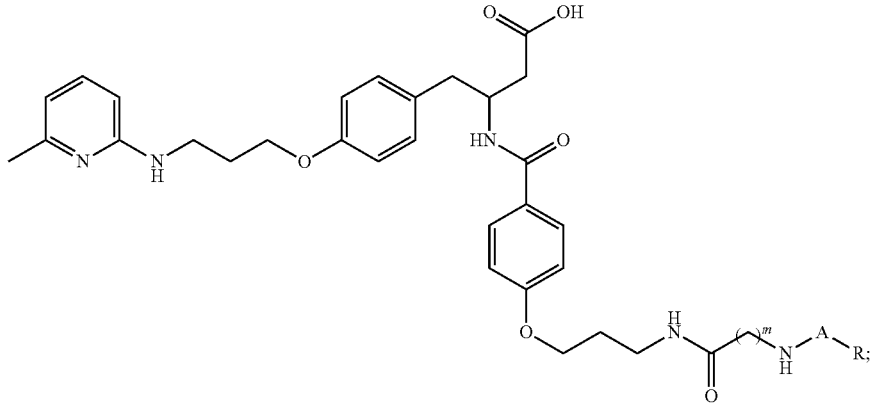

Formula (3)

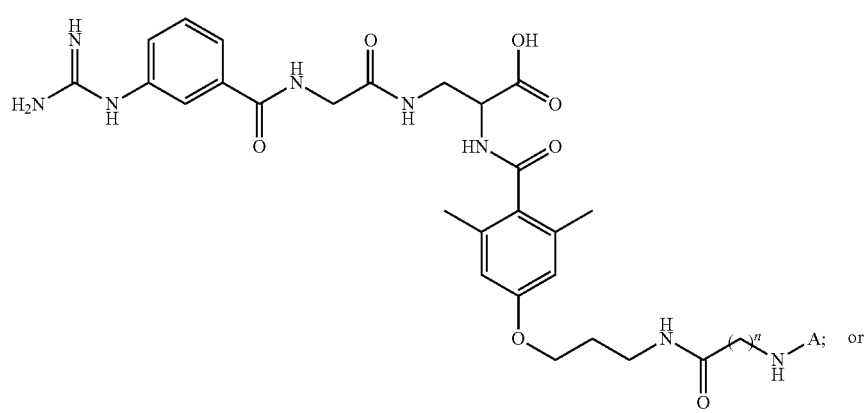

Formula (4)

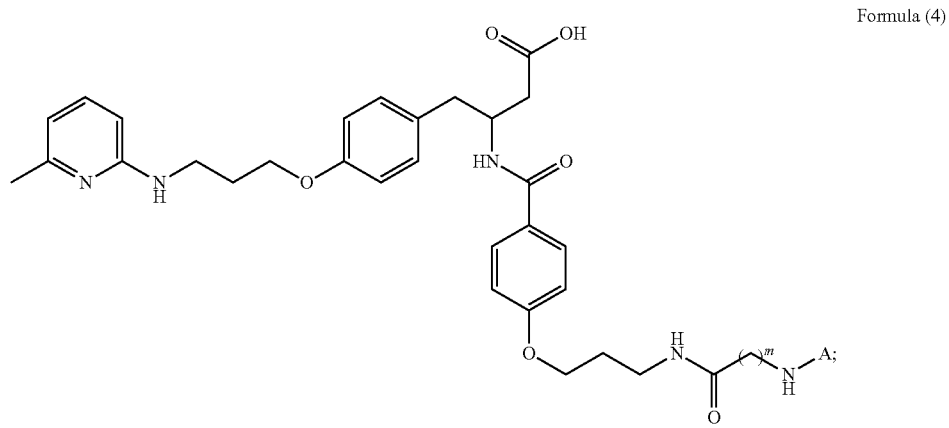

in which
A, independently of one another, stands for a coupling group selected from 1,4-phenyl ene di isothiocyanate, 1,4-phenyl ene diisocyanate, 1-isothiocyanato-4-isocyanatobenzene, N,N'-carbonyldiimidazole and/or disulfosuccinimidyltartrate; R, independently of one another, stands for chitosan or polylysine (D- or L-polylysine); wherein A is covalently linked to an amine group of R; and n and m are 1 through 20, independently of one another;

or according to the structure:

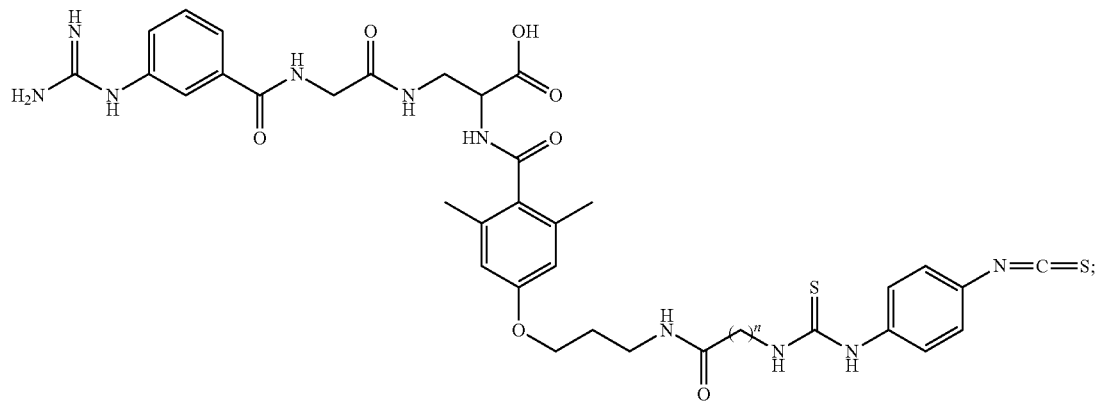

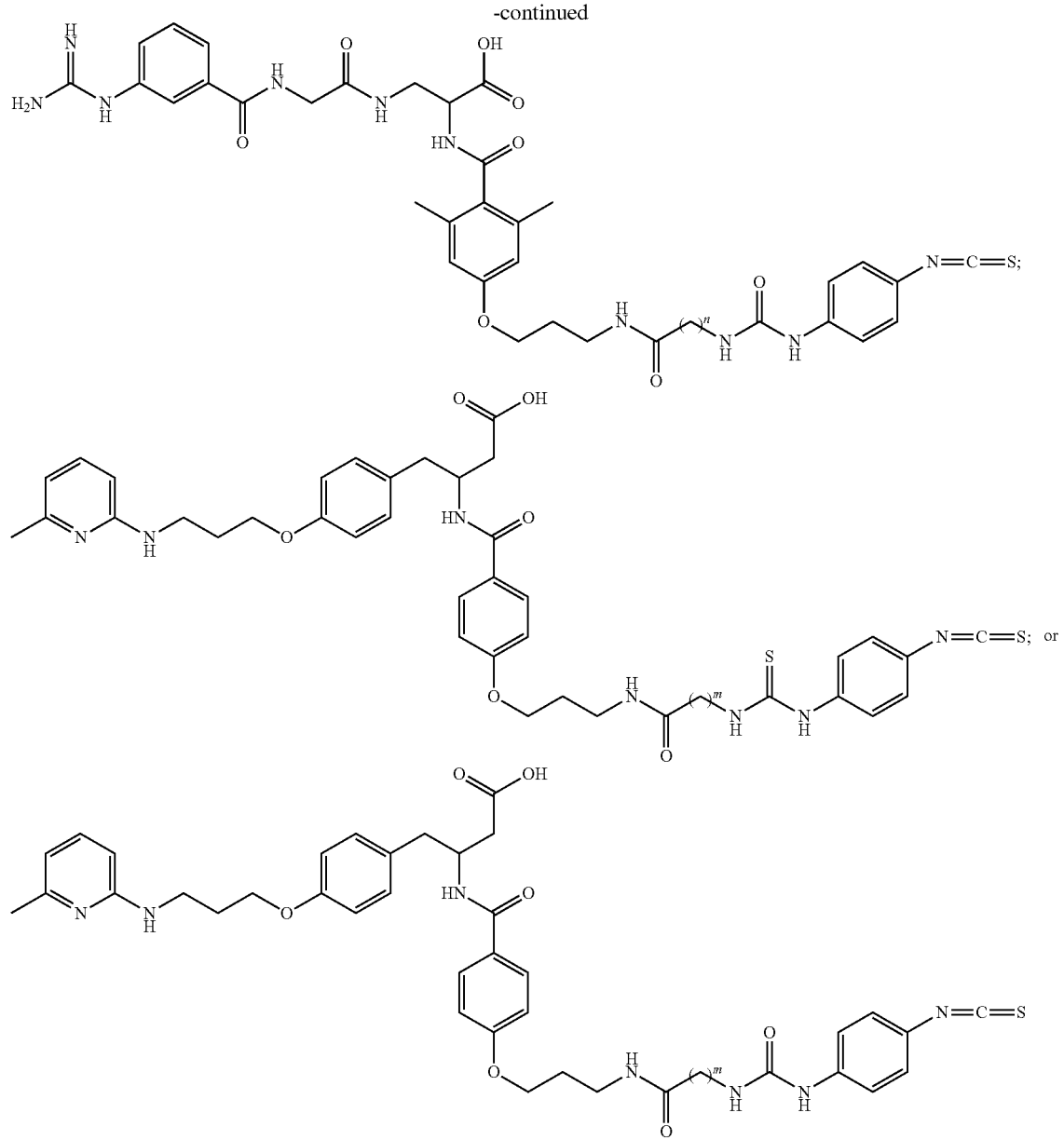
wherein n and m are 1 through 20, independently of one another.
* * * * *